United States Patent [19]

Waldner

[11] Patent Number: 4,754,033

[45] Date of Patent: Jun. 28, 1988

[54] PROCESS FOR PRODUCING PYRIDINE-2,3-DICARBOXYLIC ACID DERIVATIVES; AND NOVEL 1-AMINO-1,2,3,4-TETRAHYDROPYRIDINE-2,3-DICARBOXYLIC ACID DERIVATIVES AND 1,4-DIHYDROPYRIDINE-2,3-DICARBOXYLIC ACID DERIVATIVES

[75] Inventor: Adrian Waldner, Allschwil, Switzerland

[73] Assignee: Ciba-Geigy Corporation, Ardsley, N.Y.

[21] Appl. No.: 761,942

[22] Filed: Aug. 2, 1985

[30] Foreign Application Priority Data

Aug. 10, 1984 [CH] Switzerland ................. 3838/84

[51] Int. Cl.$^4$ ................ C07D 213/803; C07D 211/93; C07D 471/04; C07D 491/048
[52] U.S. Cl. .................... 544/127; 544/128; 544/131; 546/84; 546/92; 546/112; 546/113; 546/115; 546/116; 546/156; 546/183; 546/187; 546/193; 546/194; 546/281; 546/291; 546/296; 546/299; 546/316; 546/318; 546/321; 546/322
[58] Field of Search ............... 546/306, 316, 321, 113, 546/115, 116, 84, 92, 156, 183, 296, 291, 297, 299, 322, 318, 112, 187, 193, 194, 281; 544/127, 128, 131

[56] References Cited

FOREIGN PATENT DOCUMENTS 0041623 12/1981 European Pat. Off. .

OTHER PUBLICATIONS

Serckx-Poncin, B. et al, Tetrahedron Letters, vol. 23, No. 32, pp. 3261-3264 (1982).

Primary Examiner—Henry R. Jiles
Assistant Examiner—Dale A. Bjorkman
Attorney, Agent, or Firm—Kevin T. Mansfield; Edward McC. Roberts

[57] ABSTRACT

A process for producing pyridine-2,3-dicarboxylic acid derivatives of the formula

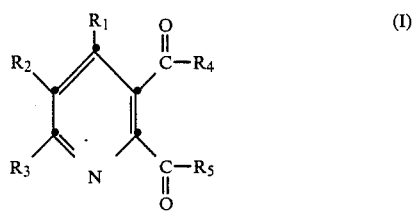

is described. The process is based on the cleavage of $HNR_{10}R_{11}$ from 1-amino-1,2,3,4-tetrahydropyridine-2,3-dicarboxylic acid derivatives of the formula II

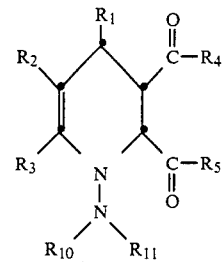

to give 1,4-dihydropyridine-2,3-dicarboxylic acid derivatives of the formula III

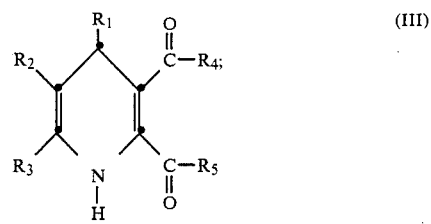

and subsequent oxidation of these compounds to obtain pyridine-2,3-dicarboxylic acid derivatives of the formula I. According to one variant of the process, the 1,4-dihydropyridine-2,3-dicarboxylic acid derivatives of the formula III are obtained directly, without isolation of the intermediately formed 1-amino-1,2,3,4-tetrahydropyridine-2,3-dicarboxylic acid derivatives of the formula II, by reaction of $\alpha,\beta$-unsaturated hydrazones of the formula IV

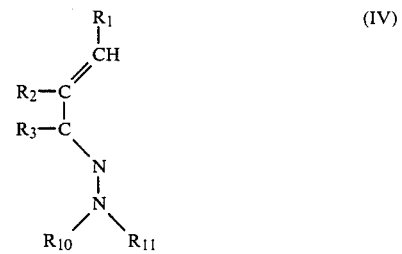

with ethene-1,2-dicarboxylic acid derivatives of the formula V

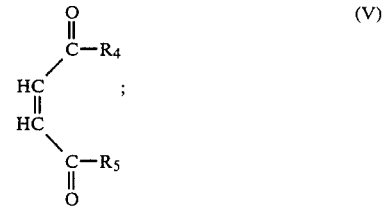

and subsequently oxidized to pyridine-2,3-dicarboxylic acid derivatives of the formula I. In the above formulae, $R_1$, $R_2$, $R_3$, $R_4$, $R_5$, $R_{10}$ and $R_{11}$ have the meanings defined in claim 1.

The pyridine-2,3-dicarboxylic acid derivatives of the formula I are intermediates for producing herbicidal active substances.

22 Claims, No Drawings

PROCESS FOR PRODUCING PYRIDINE-2,3-DICARBOXYLIC ACID DERIVATIVES; AND NOVEL 1-AMINO-1,2,3,4-TETRAHYDROPYRIDINE-2,3-DICARBOXYLIC ACID DERIVATIVES AND 1,4-DIHYDROPYRIDINE-2,3-DICARBOXYLIC ACID DERIVATIVES

The present invention relates to a process for producing pyridine-2,3-dicarboxylic acid derivatives, and to novel 1,2,3,4-tetrahydropyridine-2,3-dicarboxylic acid derivatives and 1,4-dihydropyridine-2,3-dicarboxylic acid derivatives, which occur as intermediates during the carrying out of the process.

From the European Patent Application No. 0,041,623 are known 2-(2-imidazolin-2-yl)-pyridine-3-carboxylic acid derivatives having herbicidal activity, which can be produced starting with corresponding pyridine-2,3-dicarboxylic acids and derivatives thereof. There has however not been available hitherto a process rendering possible in a simple manner the production of pyridine-2,3-dicarboxylic acids and derivatives thereof by the use of readily obtainable starting materials. It is the object of the present invention to meet this requirement by providing a process by which pyridine-2,3-dicarboxylic acids and derivatives thereof can be produced in a simple manner and in good yields from cheap and readily available starting materials.

The present invention thus relates to a process for producing pyridine-2,3-dicarboxylic acid derivatives of the formula I

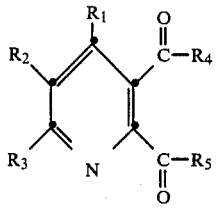

wherein $R_1$ is hydrogen, an unsubstituted or substituted, straight-chain or branched-chain alkyl, alkylthio or alkoxy group, or an unsubstituted or substituted phenyl or phenoxy group, $R_2$ has the same meaning as $R_1$ and is additionally fluorine, chlorine or bromine, $R_3$ is hydrogen or together with $R_2$ forms a trimethylene or tetramethylene group, $R_4$ and $R_5$ independently of one another are each —OH, —NH$_2$, —NHR$_6$, —NR$_6$R$_7$ or OR$_8$, where $R_6$ and $R_7$ are alkyl, cycloalkyl, allyl, methallyl, propargyl, aryl or aralkyl, or $R_6$ and $R_7$ together are alkylene or oxaalkylene, and $R_8$ is alkyl, cycloalkyl, allyl, methallyl, propargyl, aralkyl or aryl, or $R_4$ and $R_5$ together are —O— or —NR$_9$, where $R_9$ is hydrogen, unsubstituted or substituted, straight-chain or branched-chain alkyl, allyl, methallyl, propargyl, or unsubstituted or substituted cycloalkyl, aryl or aralkyl, which process comprises converting a 1-amino-1,2,3,4-tetrahydropyridine-2,3-dicarboxylic acid derivative of the formula II

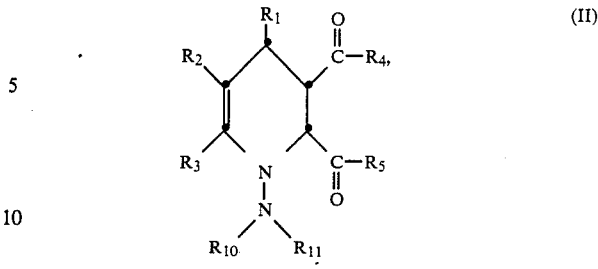

in which $R_{10}$ and $R_{11}$ individually are each alkyl, cycloalkyl, aralkyl or aryl, or together are alkylene or oxaalkylene, by treatment with an acid and/or by thermal treatment at at least 20° C. to effect the cleavage of $R_{10}R_{11}NH$, into a 1,4-dihydropyridine-2,3-dicarboxylic acid derivative of the formula III

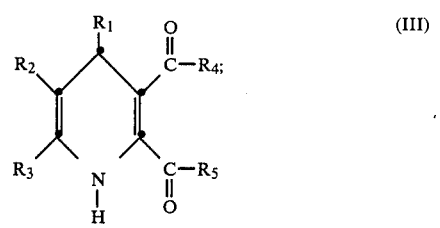

and subsequently converting this 1,4-dihydropyridine-2,3-dicarboxylic acid derivative of the formula III by oxidation into a pyridine-2,3-dicarboxylic acid derivative.

As alkyl, alkylthio and alkoxy, $R_1$ and $R_2$ in the above formulae preferably contain 1 to 6 C atoms. Suitable substituents for these radicals are hydroxyl, halogen, especially fluorine, chlorine and bromine, $C_1$-$C_4$-alkoxy, phenyl, phenoxy, cyano, carboxyl and $C_1$-$C_4$-alkoxycarbonyl. Hydroxyl and halogen are preferred substituents. Examples of these radicals are: methyl, ethyl, n-propyl, i-propyl, n-butyl, i-butyl, t-butyl, 1-pentyl, 3-pentyl, 1-hexyl, 2-hexyl, 3-hexyl, methoxy, ethoxy, n-propoxy, i-propoxy, n-butoxy, i-butoxy, t-butoxy, methylthio, ethylthio, propylthio, butylthio, hydroxymethyl, 2-hydroxyethyl, fluoromethyl, trifluoromethyl, 2-cyanoethyl, 2-chloroethyl, bromomethyl, benzyl, chlorobenzyl, methoxymethyl, ethoxymethyl and methoxyethyl.

Suitable substituents for $R_1$ and $R_2$ as phenyl and phenoxy are for example: halogen, such as F, Cl and Br, CN, $C_1$-$C_4$-alkyl, $C_1$-$C_4$-alkoxy, $C_1$-$C_4$-haloalkyl or $C_1$-$C_4$-cyanoalkyl. Examples are: methylphenyl, ethylphenyl, methoxyphenyl, ethoxyphenyl, chlorophenyl, fluorophenyl, difluorophenyl, bromophenyl, chlorophenoxy, methylphenoxy, methoxyphenoxy, fluoromethylphenyl, difluoromethylphenyl, trifluoromethylphenyl, chloromethylphenyl, cyanomethylphenyl, 2-cyanoethylphenyl, trifluoromethylphenoxy and cyanomethylphenoxy.

$R_4$ and $R_5$ independently of one another are each preferably —OH or OR$_8$, and together preferably —O— or —NR$_9$—. As alkyl, $R_6$ and $R_7$ preferably contain 1 to 6, particularly 1 to 4, C atoms. $R_6$ and $R_7$ as cycloalkyl are preferably cyclopentyl or cyclohexyl. $R_6$ and $R_7$ together as alkylene are preferably pentamethylene or tetramethylene, and as oxaalkylene preferably 3-oxapentylene. As aryl or aralkyl, $R_6$ and $R_7$ are preferably $C_6$-$C_{16}$-aryl or $C_7$-$C_{16}$-aralkyl, in particular phenyl or benzyl, which can be substituted like $R_1$ and $R_2$ as phenyl.

As alkyl, $R_8$ can be straight-chain or branched-chain, and preferably contains 1 to 6 C atoms. $R_8$ as cycloalkyl is preferably cyclopentyl or cyclohexyl. As aryl or aralkyl, $R_8$ is preferably phenyl or benzyl which can be substituted for example by $C_1$-$C_4$-alkyl, $C_1$-$C_4$-alkoxy or halogen, such as fluorine, chlorine or bromine.

Suitable substituents for $R_9$ are for example: —OH, —OR$_{12}$, —SR$_{12}$, wherein $R_{12}$ is $C_1$-$C_6$-alkyl, cyclohexyl or phenyl, —COOH, —COOR$_8$, —OCOR$_{12}$, —CONH$_2$, —CONHR$_6$, —CONR$_6$R$_7$ and halogen, for example fluorine, chlorine, or bromine, and cyano. As alkyl, $R_9$ preferably contains 1 to 6 C atoms. Examples have been mentioned in the foregoing.

As cycloalkyl, $R_9$ is preferably cyclohexyl or cyclopentyl. Examples of $R_9$ as substituted radicals are: hydroxymethyl, 2-hydroxyethyl, methoxymethyl, methoxyethyl, ethoxyethyl, phenoxyethyl, dimethylamino, diethylamino, methoxycarbonylmethyl, ethoxycarbonylethyl, propoxycarbonylmethyl, phenoxycarbonylmethyl, benzoyloxymethyl, acetyloxyethyl, methylaminocarbonylmethyl, dimethylaminocarbonylethyl, chloromethyl, 2-chloroethyl, cyanomethyl, 2-cyanoethyl, 2-cyanopropyl, 2-[2-cyano-3-methyl]butyl and 2-[2-carbamoyl-3-methyl]butyl.

$R_4$ and $R_5$ are preferably —OH, —NH$_2$, —NHR$_6$, —NR$_6$R$_7$ or —OR$_8$, wherein $R_6$ and $R_7$ are $C_1$-$C_6$-alkyl, cyclopentyl, cyclohexyl, phenyl or benzyl, or $R_6$ and $R_7$ together are tetramethylene, pentamethylene or 3-oxapentylene, or $R_4$ and $R_5$ together are —O— or —NR$_9$—, wherein $R_9$ is $C_1$-$C_6$-alkyl, $C_1$-$C_6$-cyanoalkyl, $C_1$-$C_6$-aminocarbonylalkyl or phenyl.

As alkyl, $R_{10}$ and $R_{11}$ can be straight-chain or branched-chain, and preferably contain 1 to 6, especially 1 to 4, C atoms. Particularly preferred radicals $R_{10}$ and $R_{11}$ are ethyl or methyl. $R_{10}$ and $R_{11}$ as cycloalkyl are preferably cyclopentyl or cyclohexyl, as aryl preferably phenyl, and as aralkyl preferably phenylalkyl, in particular benzyl. In a preferred embodiment, $R_{10}$ is phenyl and $R_{11}$ is $C_1$-$C_6$-alkyl. $R_{10}$ and $R_{11}$ together as alkylene are preferably tetramethylene or pentamethylene, and as oxaalkylene preferably 3-oxapentylene.

In a preferred embodiment, $R_4$ and $R_5$ are a radical of the formula

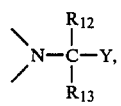

wherein Y is —CN or —CONH$_2$, and $R_{12}$ and $R_{13}$ independently of one another are each a hydrogen atom or straight-chain or branched-chain $C_1$-$C_6$-alkyl. $R_{12}$ and $R_{13}$ are preferably straight-chain or branched-chain $C_1$-$C_4$-alkyl.

In a particular preferred subgroup, $R_4$ and $R_5$ are:

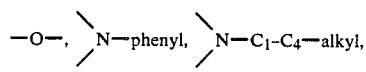

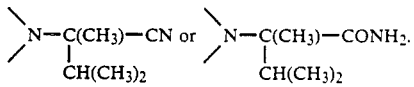

The process according to the invention is advantageously performed in an inert solvent. Suitable solvents are those which are inert to the reactants. Particularly suitable are polar, protic and aprotic solvents, which can be used individually or in mixtures of at least two solvents. Examples are: ethers, such as dibutyl ether, tetrahydrofuran, dioxane, ethylene glycol, dimethyleneethylene glycol, diethyldiethylene glycol, dimethyltriethylene glycol, halogenated hydrocarbons, such as methylene chloride, chloroform, 1,2-dichloroethane, 1,1,1-trichloroethane, 1,1,2,2-tetrachloroethane, carboxylic esters and lactones, such as ethyl acetate, methyl propionate, ethyl benzoate, 2-methoxyethyl acetate, Γ-butyrolactone and ε-valerolactone, carboxylic amides and lactams, such as formamide, acetamide, N-methylformamide, N,N-dimethylformamide, N,N-diethylformamide, N,N-dimethylacetamide, N,N-diethylacetamide, Γ-butyrolactam, N-methylpyrrolidone, tetramethylurea, hexamethylphosphoric acid triamide, sulfoxides, such as dimethylsulfoxide, sulfones, such as dimethylsulfone, diethylsulfone, trimethylenesulfone, tetramethylenesulfone, tert. amines, such as trimethylamine, triethylamine, N-methylpyrrolidine, N-methylpiperidine, N-methylmorpholine, substituted benzenes, such as toluene, chlorobenzene, nitrobenzene, nitriles, such as acetonitrile, and alcohols, such as methanol, ethanol and propanol.

The 1-amino-1,2,3,4-tetrahydropyridine-2,3-dicarboxylic acid derivatives of the formula II are in part known and can be produced, using processes known per se, by reaction of α,β-unsaturated hydrazones of the formula IV

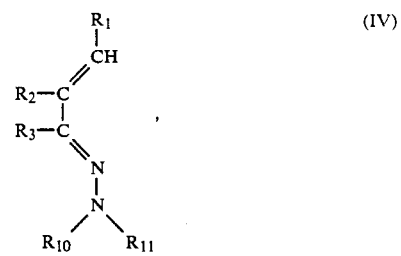

in which $R_1$, $R_2$, $R_3$, $R_{10}$ and $R_{11}$ have the meanings defined in the foregoing, with ethene-1,2-dicarboxylic acid derivatives of the formula V

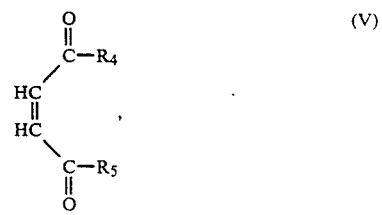

in which $R_4$ and $R_5$ have the meanings defined in the foregoing (cf. Tetrahedron Letters, Vol. 23, No. 32, pp. 3261-3264 (1982)).

The novel 1-amino-1,2,3,4-tetrahydropyridine-2,3-dicarboxylic acid derivatives are likewise subject matter of the present invention. They correspond to the formula II according to the above definition with the exception of those compounds in which $R_4$ and $R_5$ are OH, $OCH_3$ or $OC_2H_5$, or together are —O— when simultaneously $R_1$ is hydrogen and $R_2$ is methyl. Preferred compounds of the formula II are those wherein $R_4$ and $R_5$ together are $-NR_9-$. They correspond to the formula IIa

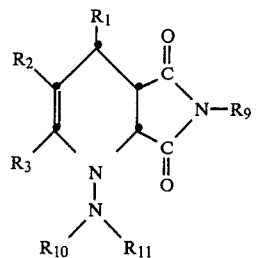

(IIa)

in which $R_1$, $R_2$, $R_3$, $R_9$, $R_{10}$ and $R_{11}$ have the meanings defined in the foregoing.

The 1,4-dihydropyridine-2,3-dicarboxylic acid derivatives of the formula III are likewise novel and form further subject matter of the present invention. Preferred compounds of the formula III are those wherein $R_4$ and $R_5$ together are —O— or $-NR_9-$. These compounds correspond to the formulae IIIa and IIIb

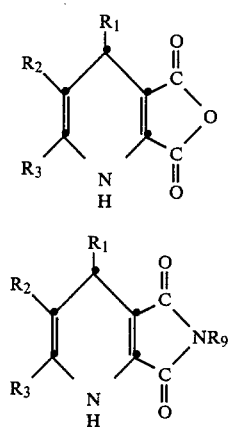

wherein $R_1$, $R_2$, $R_3$ and $R_9$ have the meanings defined in the foregoing.

The cleavage of $HNR_{10}R_{11}$ from 1-amino-1,2,3,4-tetrahydropyridine-2,3-dicarboxylic acid derivatives of the formula II can be performed in a wide temperature range. Suitable temperatures are between 20° and 200° C. The reaction is preferably carried out at a temperature of between 40° and 150° C. in an inert solvent. Preferred solvents are toluene and ethanol. Suitable acids in the presence of which the amine cleavage can be effected are in particular organic acids, such as formic acid, acetic acid, propionic acid or oxalic acid. Especially suitable are acid silicates, for example silica gel. The reaction is performed particularly advantageously by heating a 1-amino-1,2,3,4-tetrahydropyridine-2,3-dicarboxylic acid derivative with approximately the double amount of silica gel in toluene at the reflux temperature.

By use of one variant of the process according to the invention, the 1,4-dihydropyridine-2,3-dicarboxylic acid derivatives of the formula III, obtainable by cleavage of $HNR_{10}R_{11}$ from the 1-amino-1,2,3,4-tetrahydropyridine-2,3-dicarboxylic acid derivatives of the formula II, can also be produced directly by reaction of $\alpha,\beta$-unsaturated hydrazones of the formula IV with ethylene-1,2-dicarboxylic acid derivatives of the formula V, without isolation of the intermediately formed 1-amino-1,2,3,4-tetrahydropyridine-2,3-dicarboxylic acid derivatives of the formula II. This variant of the process comprises heating an $\alpha,\beta$-unsaturated hydrazone of the formula IV and an ethene-1,2-dicarboxylic acid derivative of the formula V in an inert solvent at a temperature of between 40° and 150° C.; and subsequently converting the formed 1,4-dihydropyridine-2,3-dicarboxylic acid derivative of the formula III by oxidation into a pyridine-2,3-dicarboxylic acid derivative of the formula I. Particularly suitable solvents are acetonitrile or lower alkanols, such as methanol, ethanol or propanol. Depending on the temperature, the reaction time is as a rule 10–25 hours, especially 15–20 hours. These reaction times can however be considerably shortened by addition of one of the aforementioned acids, particularly by the addition of an acid silicate.

Suitable oxidising agents for converting a 1,4-dihydropyridine-2,3-dicarboxylic acid derivative of the formula III into a pyridine-2,3-dicarboxylic acid derivative of the formula I are for example: oxygen, hydrogen peroxide, manganese dioxide (pyrolusite), chromic acid, or solutions of iodine in an organic solvent, and particularly air. Chromic acid can be used advantageously in the form of sodium or potassium dichromate, optionally together with organic acids. Oxidation with air can advantageously be performed in the presence of a catalyst, such as palladium or platinum. The reaction is carried out in particular in an inert solvent in the presence of organic acids, especially acetic acid, in which process the organic acids can serve directly as solvents. The reaction temperature is in general between 20° and 200° C., preferably between 30° and 100° C.

The oxidation of 1,4-dihydropyridine-2,3-carboxylic acid derivatives of the formula III to pyridine-2,3-dicarboxylic acid derivatives of the formula I can be effected in a particularly advantageous manner by heating with the essentially equimolar amount of manganese dioxide in acetic acid. With this procedure, the reaction temperatures are as a rule 50°–100° C., and the reaction times ½ to 1 hour.

By the use of corresponding starting materials, the compounds of the formula I can be produced directly by the process according to the invention. It is however also possible to convert directly resulting compounds of the formula I, by forming derivatives within the scope defined by the formula I, into other compounds of the formula I. Thus, for example, it is possible to produce from anhydrides of the formula I the free acids and semi-esters, esters, semi-amides and amides thereof.

It is possible to obtain by the process according to the invention with the use of readily available starting products, by a quick method of synthesis under mild reaction conditions, pure pyridine-2,3-dicarboxylic acid derivatives of the formula I in high levels of yield. The process is particularly suitable for being carried out on a commercial scale.

The compounds of the formula I are valuable intermediates, particularly for producing herbicides such as those described for example in the European Patent Applications Nos. EP-A No. 0,041,623, EP-A No. 0,041,624 and EP-A No. 0,095,104.

The following Examples further illustrate the present invention.

EXAMPLE a

Production of

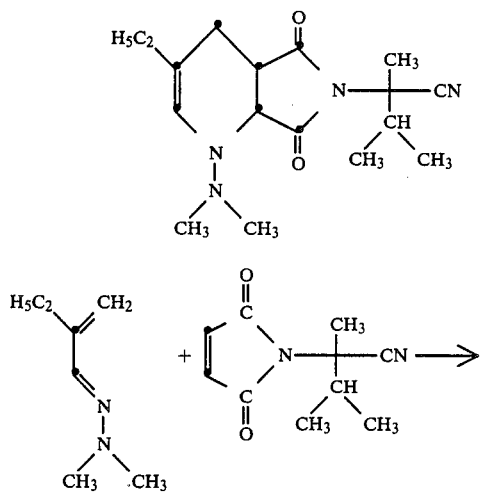

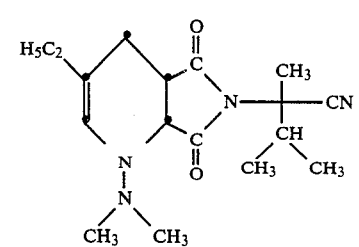

16.5 g of hydrazone and 10.8 g of imide are heated in 100 ml of acetonitrile for 3½ hours at 60° C. After concentration by evaporation, the yellow solution yields quantitatively an orange oil.

NMR(CDCl₃): 6.0 (H—C=C); 2.55 (N(CH₃)₂); 3.95 (N—CH—C=O).

EXAMPLE b

There are obtained the following compounds by heating equimolar amounts of hydrazone and imide for 1–3 hours in the 2–5-fold amount of ethanol at 70° C., and subsequently evaporating off the solvent.

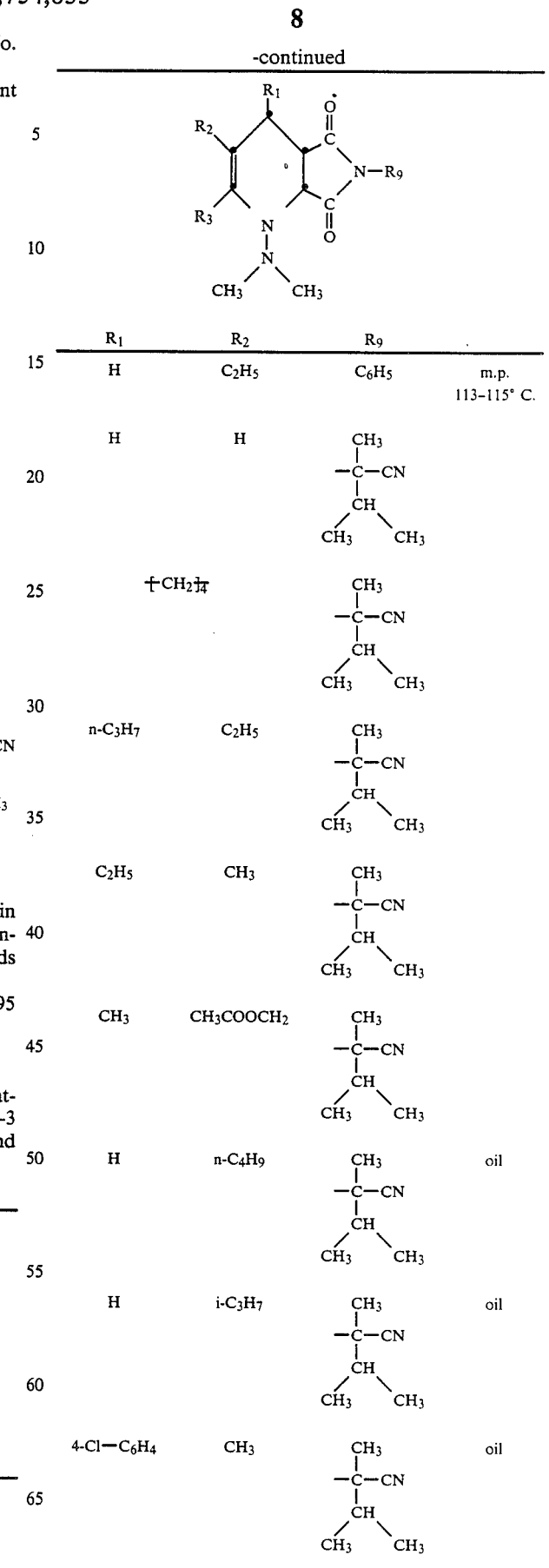

-continued

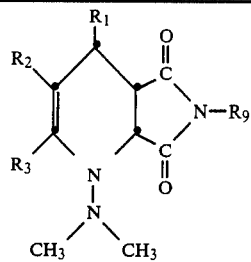

| R₁ | R₂ | R₉ | |
|---|---|---|---|
| H | CH₃ | -C(CH₃)(CN)-CH(CH₃)₂ | oil |
| CH₃ | F | -C(CH₃)(CN)-CH(CH₃)₂ | oil |
| H | F | -C(CH₃)(CN)-CH(CH₃)₂ | |

Example 1

(a) Production of

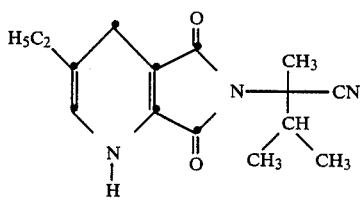

27.3 g of tetrahydropyridine according to Example (a) are dissolved in 300 ml of toluene; 30 g of silica gel are added, and the mixture is then heated to reflux temperature. After 1½ hours, the mixture is concentrated by evaporation, and eluted through a small amount of silica gel with toluene/ethyl acetate (4:1). The eluate is concentrated by evaporation to yield 19 g of red crystals, which slowly decompose.

NMR (CDCl₃): 5.90 (H=C); 6.70 (NH, interchangeable with D₂O).

(b) Production of

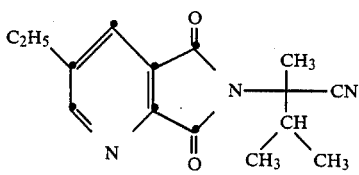

6.0 g of dihydropyridine are dissolved in 40 ml of acetic acid, and the solution is heated to 45° C. Air is passed through for half an hour, in the course of which a yellow solution is formed. This is concentrated by evaporation, and distributed between chloroform and 2N sodium carbonate. The organic phase is dried, and concentrated by evaporation, The residue is recrystallised from ether to thus obtain 3.1 g of product, m.p. 73°–73.5° C.

Elementary analysis: Calculated: C 66.40 H 6.32 N 15.49; Found: C 66.30 H 6.35 N 15.46.

Example 2

The following 1,4-dihydropyridine-2,3-dicarboxylic acid derivatives are produced in a manner analogous to that of Example 1a:

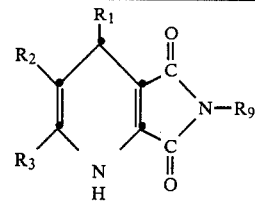

| R₁ | R₂ | R₉ | m.p. (°C.) |
|---|---|---|---|
| n-C₃H₇ | CH₃ | C₆H₅ | 144–150 |
| H | n-C₃H₇ | C₆H₅ | 174–176 |
| ─(CH₂)₄─ | | C₆H₅ | 170–173 |
| C₆H₅ | C₂H₅ | C₆H₅ | 171–173 |
| CH₃ | CH₃COOCH₂ | C₆H₅ | 125–128 |
| 3-NO₂C₆H₄ | CH₃ | C₆H₅ | 199–202 |
| H | C₂H₅ | C₆H₅ | |
| 2,3-Cl─C₆H₅ | C₂H₅ | C₆H₅ | |
| H | n-C₃H₇ | -C(CH₃)(CN)-CH(CH₃)-CH₃ | oil |
| C₆H₅ | C₂H₅ | -C(CH₃)(CN)-CH(CH₃)-CH₃ | 135–136 |
| C₂H₅ | CH₃ | -C(CH₃)(CN)-CH(CH₃)-CH₃ | oil |
| n-C₃H₇ | C₂H₅ | -C(CH₃)(CN)-CH(CH₃)-CH₃ | oil |
| ─(CH₂)₄─ | | -C(CH₃)(CN)-CH(CH₃)-CH₃ | oil |
| C₆H₅ | CH₃ | -C(CH₃)(CN)-CH(CH₃)-CH₃ | 168–169 |

-continued (Structure: dihydropyridine with R1, R2, R3 substituents, N-H in ring, N-R9 in imide)

| R1 | R2 | R9 | m.p. (°C.) |
|---|---|---|---|
| CH3 | CH3COOCH2 | -C(CH3)(CN)-CH(CH3)-CH3 | oil |
| H | n-C4H9 | -C(CH3)(CN)-CH(CH3)-CH3 | oil |
| H | n-C3H7 | -C(CH3)(CN)-CH(CH3)-CH3 | oil |
| 4-Cl—C6H4 | CH3 | -C(CH3)(CN)-CH(CH3)-CH3 | oil |
| 3-NO2—C6H4 | CH3 | -C(CH3)(CN)-CH(CH3)-CH3 | 161–162 |
| C2H5 | CH3 | -C(CH3)(CN)-CH(CH3)-CH3 | oil |
| CH3 | F | -C(CH3)(CN)-CH(CH3)-CH3 | 145–147 |
| H | n-C3H7 | -C(CH3)(CONH2)-CH(CH3)(CH3) | resin |
| H | F | -C(CH3)(CN)-CH(CH3)(CH3) | oil |

-continued

| R1 | R2 | R9 | m.p. (°C.) |
|---|---|---|---|
| H | CH3 | -C(CH3)-CH(CH3)(CH3) |  |

Example 3

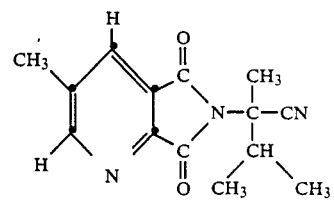

140.7 g of dihydropyridine (cf. Ex. 2, last line) are suspended in 800 ml of acetic acid, and the suspension is heated to 60° C. There are then added portionwise 71 g of manganese dioxide, and stirring is continued at 60° C. for half an hour. The mixture is subsequently cooled to room temperature, filtered, and concentrated by evaporation. The residue is distributed between chloroform and aqueous sodium carbonate solution. The organic phase is separated and, after drying over magnesium sulfate, concentrated by evaporation. The residue is washed with ether to thus obtain 119 g of the above compound in the form of a beige powder, m.p. 119°–120° C.

The following compounds are produced in an analogous manner:

Production of (Structure: pyridine ring with R1, R2, R3 substituents and N-R9 imide)

| R1 | R2 | R3 | R9 | m.p. (°C.) |
|---|---|---|---|---|
| n-C3H7 | CH3 | H | C6H5 | 177–179 |
| H | n-C3H7 | H | C6H5 | 153–154 |
| | ⟨CH2⟩4 | H | C6H5 | 149–150 |
| C6H5 | C2H5 | H | C6H5 |  |
| CH3 | CH3COOCH2 | H | C6H5 | 118–120 |
| H | C2H5 | H | C6H5 | 190–191 |
| CH3 | CH3 | H | C6H5 | 244–246 |
|  | ⟨CH2⟩4 | H | C6H5 | 149–150 |

-continued structure with R1, R2, R3, R9 on maleimide-pyridine fused system

| R1 | R2 | R3 | R9 | m.p. (°C.) |
|---|---|---|---|---|
| H | n-C3H7 | H | $-\underset{CH_3}{\underset{|}{C}}(CN)-\underset{CH_3}{CH}-CH_3$ with CH3 | 59–60 |
| C2H5 | CH3 | H | same isobutyronitrile-type group | 105–107 |
| n-C3H7 | C2H5 | H | same group | 76–77 |
| ‒(CH2)4‒ | | H | same group | 121–125 |
| C6H5 | CH3 | H | same group | 169–170 |
| C6H5 | CH3 | H | same group | 142–143 |
| CH3 | CH3COOCH2 | H | same group | oil |
| H | n-C4H9 | H | same group | oil |
| H | i-C3H7 | H | same group | 95–96 |

| R1 | R2 | R3 | R9 | m.p. (°C.) |
|---|---|---|---|---|
| 4-Cl—C6H4 | CH3 | H | $-\underset{CH_3}{\underset{|}{C}}(CN)-CH(CH_3)_2$ | 112–114 |
| 3-NO2—C6H4 | CH3 | H | same group | 164–166 |
| H | CH3 | H | same group | 119–120 |
| CH3 | F | H | same group | oil |
| H | C2H5 | H | $-\underset{CH_3}{\underset{|}{C}}(CO-NH_2)-CH(CH_3)_2$ | 90–94 |
| H | F | H | $-\underset{CH_3}{\underset{|}{C}}(CN)-CH(CH_3)_2$ | |

Example 4

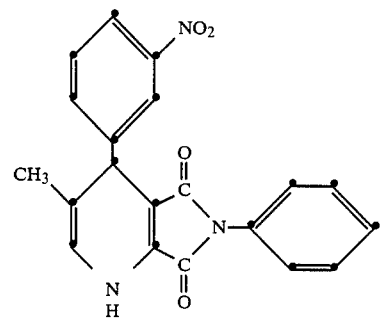

30.3 g of the N,N-dimethylhydrazone of 3-(3-nitrophenyl)-2-methyl-2-propen-1-al (3-(3-nitrophenyl)-methacrolein) and 22.5 g of N-phenylmaleinimide in 260 ml of acetonitrile are heated for 16 hours at the reflux temperature. The reaction mixture is subsequently treated with active charcoal and filtered. The solvent is then evaporated off, and the residue is washed with ether/hexane and concentrated by evaporation. The yield is 20.5 g of the above compound, m.p. 199°-202° C.

There is obtained in an analogous manner, from the N,N-dimethylhydrazone of 3-(3-nitrophenyl)-methacrolein and N-(1-cyano-1,2-dimethylpropyl)-maleinimide, the compound of the formula

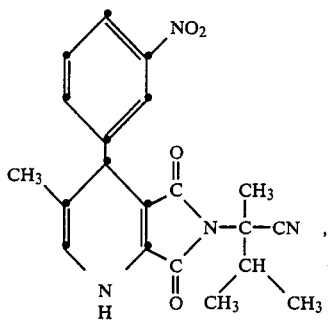

m.p. 161°-162° C.

What is claimed is:

1. A process for producing pyridine-2,3-dicarboxylic acid derivatives of the formula I

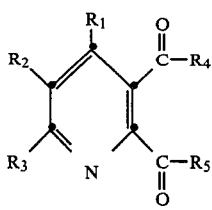

wherein

R$_1$ is hydrogen or C$_1$-C$_6$alkyl, C$_1$-C$_6$alkylthio or C$_1$-C$_6$alkoxy which are unsubstituted or substituted by hydroxy, halogen, C$_1$-C$_4$alkoxy, phenyl, phenoxy, cyano, carboxyl or C$_1$-C$_4$-alkoxycarbonyl; or R$_1$ is phenyl or phenoxy, unsubstituted or substituted by halogen, cyano, C$_1$-C$_4$alkyl, C$_1$-C$_4$alkoxy, C$_1$-C$_4$haloalkyl or C$_1$-C$_4$cyanoalkyl, R$_2$ has the same meaning as R$_1$ and is additionally fluorine, chlorine or bromine, R$_3$ is hydrogen or together with R$_2$ forms a trimethylene or tetramethylene group, R$_4$ and R$_5$ independently of one another are —OH, —NH$_2$, —NHR$_6$, —NR$_6$R$_7$ or —OR$_8$, where R$_6$ and R$_7$ are C$_1$-C$_6$alkyl, C$_5$-C$_6$cycloalkyl, allyl, methallyl, propargyl, unsubstituted C$_6$-C$_{16}$aryl or C$_7$-C$_{16}$aralkyl or C$_6$-C$_{16}$aryl or C$_7$-C$_{16}$aralkyl which are substituted by halogen, cyano, C$_1$-C$_4$alkyl, C$_1$-C$_4$alkoxy, C$_1$-C$_4$haloalkyl or C$_1$-C$_4$cyanoalkyl, or R$_6$ and R$_7$ together are C$_4$-C$_5$alkylene or 3-oxapentalene, and R$_8$ is C$_1$-C$_6$alkyl, C$_5$-C$_6$cycloalkyl, allyl, methallyl, propargyl unsubstituted phenyl or benzyl or phenyl or benzyl which is substituted by C$_1$-C$_4$alkyl, C$_1$-C$_4$alkoxy or halogen, or R$_4$ and R$_5$ taken together are —O— or —NR$_9$— where R$_9$ is unsubstituted C$_1$-C$_6$alkyl or C$_1$-C$_6$alkyl substituted by —OH, —OR$_{12}$ or —SR$_{12}$, wherein R$_{12}$ is C$_1$-C$_6$alkyl, cyclohexyl or phenyl, —COOH, —COOR$_8$, —OCOR$_{12}$, —CONH$_2$, —CONHR$_6$, —CONR$_6$R$_7$, halogen or cyano, or is allyl, methallyl, propargyl unsubstituted phenyl or benzyl or phenyl or benzyl which are substituted by C$_1$-C$_7$alkyl, C$_1$-C$_4$alkoxy or halogen, which process comprises converting a 1-amino-1,2,3,4-tetrahydropyridine-2,3-dicarboxylic acid derivative of the formula II

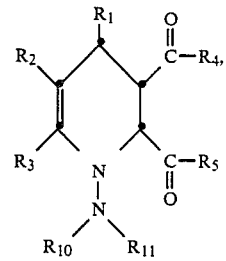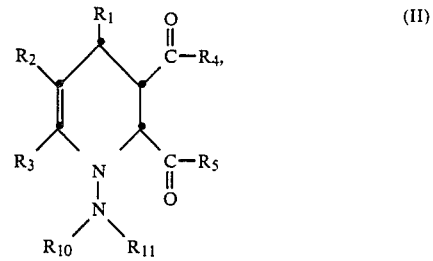

in which R$_{10}$ and R$_{11}$ individually are each C$_1$-C$_6$alkyl, C$_5$-C$_6$cycloalkyl, aralkyl or aryl, or together are C$_4$-C$_5$alkylene or 3-oxapentylene by treatment with an acid or by thermal treatment at least 20° C. to effect the cleavage of R$_{10}$R$_{11}$NH, into a 1,4-dihydropyridine-2,3-dicarboxylic acid derivative of the formula III and subsequently converting this 1,4-dihydropyridine-2,3-dicarboxylic acid derivative of the formula III by oxidation into a pyridine-2,3-dicarboxylic acid derivative.

2. A process according to claim 1, wherein the conversion of the 1-amino-1,2,3,4-tetrahydropyridine-2,3-dicarboxylic acid derivative of the formula II into the 1,4-dihydropyridine-2,3-dicarboxylic acid derivative of the formula III is performed at temperatures of between 20° and 200° C.

3. A process according to claim 2, wherein the conversion of the 1-amino-1,2,3,4-tetrahydropyridine-2,3-dicarboxylic acid derivative of the formula II into the 1,4-dihydropyridine-2,3-dicarboxylic acid derivative of the formula III is performed at a temperature of between 40° and 150° C. in an inert solvent.

4. A process according to claim 3, wherein the inert solvent used is toluene or ethanol.

5. A process according to claim 1, wherein the conversion of the 1-amino-1,2,3,4-tetrahydropyridine-2,3-dicarboxylic acid derivative of the formula II into the 1,4-dihydropyridine-2,3-dicarboxylic acid derivative of the formula III is performed in the presence of an organic acid selected from the group comprising formic acid, acetic acid and propionic acid.

6. A process according to claim 1, wherein the conversion of the 1-amino-1,2,3,4-tetrahydropyridine-2,3-dicarboxylic acid derivative of the formula II into the 1,4-dihydropyridine-2,3-dicarboxylic acid derivative of the formula III is performed in the presence of an acid silicate.

7. A process according to claim 1, wherein the conversion of the 1-amino-1,2,3,4-tetrahydropyridine-2,3-dicarboxylic acid derivative of the formula II into the 1,4-dihydropyridine-2,3-dicarboxylic acid derivative of the formula III is performed by heating the 1-amino-1,2,3,4-tetrahydropyridine-2,3-dicarboxylic acid derivative of the formula II with approximately the double amount of silica gel in toluene at the reflux temperature.

8. A process for producing pyridine-2,3-dicarboxylic acid derivatives of the formula I according to claim 1, which process comprises heating an α,β-unsaturated hydrazone of the formula IV

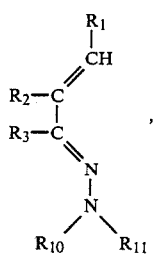
(IV)

in which $R_1$, $R_2$, $R_3$, $R_{10}$ and $R_{11}$ have the meanings defined under the formulae I and II, and an ethene-1,2-dicarboxylic acid derivative of the formula V

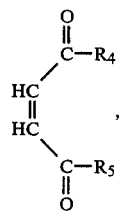
(V)

in which $R_4$ and $R_5$ have the meanings defined under the formula I, in an inert solvent at a temperature of between 40° and 150° C.; and subsequently converting the formed 1,4-dihydropyridine-2,3-dicarboxylic acid derivative of the formula III by oxidation into a pyridine-2,3-dicarboxylic acid derivative of the formula I.

9. A process according to claim 8, wherein said inert solvent is acetonitrile or a lower alkanol.

10. A process according to claim 1 or 8, wherein the oxidising agent used for converting the 1,4-dihydropyridine-2,3-dicarboxylic acid derivative of the formula III into a pyridine-2,3-dicarboxylic acid derivative of the formula I is selected from the group comprising: air, oxygen, hydrogen peroxide, manganese dioxide and chromic acid.

11. A process according to claim 10, wherein the oxidation of the 1,4-dihydropyridine-2,3-dicarboxylic acid derivative of the formula III to the pyridine-2,3-dicarboxylic acid derivative of the formula I is performed with air.

12. A process according to claim 10, wherein the oxidation of the 1,4-dihydropyridine-2,3-dicarboxylic acid derivative of the formula III to the pyridine-2,3-dicarboxylic acid derivative of the formula I is performed in the presence of an organic acid at between 20° and 200° C.

13. A process according to claim 10, wherein the oxidation of the 1,4-dihydropyridine-2,3-dicarboxylic acid derivative of the formula III to the pyridine-2,3-dicarboxylic acid derivative of the formula I is performed by heating with the essentially equimolar amount of manganese dioxide in acetic acid at a temperature of between 50° and 100° C.

14. A process according to claims 1 or 8, wherein there is used a 1-amino-1,2,3,4-tetrahydropyridine-2,3-dicarboxylic acid derivative of the formula II or an ethene-1,2-dicarboxylic acid derivative of the formula V in which $R_4$ and $R_5$ are a radical of the formula

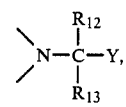

wherein Y is —CN or —CONH$_2$, and $R_{12}$ and $R_{13}$ independently of one another are each a hydrogen atom, or straight-chain or branched-chain $C_1$-$C_6$-alkyl.

15. A process according to claims 1 or 8, wherein there is used a 1-amino-1,2,3,4-tetrahydropyridine-2,3-dicarboxylic acid derivative of the formula II or an ethene-1,2-dicarboxylic acid derivative of the formula V, wherein $R_4$ and $R_5$ together are:

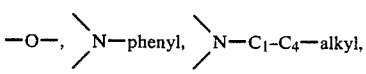

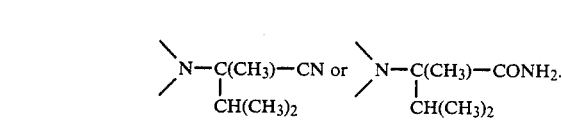

16. A process according to claims 1 or 8, wherein there are produced pyridine-2,3-dicarboxylic acid derivatives of the formula I in which $R_1$ is hydrogen or methyl, $R_2$ is hydrogen, $C_1$-$C_6$-alkyl, fluorine, chlorine, bromine, $C_1$-$C_6$-alkoxy, $C_1$-$C_4$-alkylthio, phenoxy, $C_1$-$C_6$-hydroxyalkyl, $C_1$-$C_6$-haloalkyl, or phenyl unsubstituted or substituted by $C_1$-$C_4$-alkyl, $C_1$-$C_4$-alkoxy or halogen, $R_3$ is hydrogen, and $R_4$ and $R_5$ individually are each —OH or —OR$_8$, or together are —O— or —NR$_9$—.

17. A process according to claims 1 or 8, wherein there are produced pyridine-2,3-dicarboxylic acid derivatives of the formula I in which $R_1$ is hydrogen, $R_2$ is $C_1$-$C_6$-alkyl, $R_3$ is hydrogen, and $R_4$ and $R_5$ individually are each —OH or —OR$_8$, or together are a group

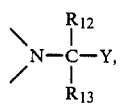

wherein $R_8$, $R_{12}$ and $R_{13}$ each have the meanings defined under the formulae I and II, and Y is a cyano group or a carbamoyl group.

18. 1-Amino-1,2,3,4-tetrahydropyridine-2,3-dicarboxylic acid derivatives of the formula II

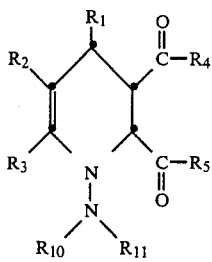

(II)

wherein $R_1$ is hydrogen or $C_1$-$C_6$alkyl, $C_1$-$C_6$alkylthio or $C_1$-$C_6$alkoxy which are unsubstituted or substituted by hydroxy, halogen, $C_1$-$C_4$alkoxy, phenyl, phenoxy, cyano, carboxyl or $C_1$-$C_4$-alkoxycarbonyl; or $R_1$ is phenyl or phenoxy, unsubstituted or substituted by halogen, cyano, $C_1$-$C_4$alkyl, $C_1$-$C_4$alkoxy, $C_1$-$C_4$haloalkyl or $C_1$-$C_4$cyanoalkyl, $R_2$ has the same meaning as $R_1$ and is additionally fluorine, chlorine or bromine, $R_3$ is hydrogen or together with $R_2$ forms a trimethylene or tetramethylene group, $R_4$ and $R_5$ independently of one another are —OH, —NH$_2$, —NHR$_6$, —NR$_6$R$_7$ or —OR$_8$, where $R_6$ and $R_7$ are $C_1$-$C_6$alkyl, $C_5$-$C_6$cycloalkyl, allyl, methallyl, propargyl, unsubstituted $C_6$-$C_{16}$aryl or $C_7$-$C_{16}$aralkyl or $C_6$-$C_{16}$aryl or $C_7$-$C_{16}$aralkyl which are substituted by halogen, cyano, $C_1$-$C_4$alkyl, $C_1$-$C_4$alkoxy, $C_1$-$C_4$haloalkyl or $C_1$-$C_4$cyanoalkyl, or $R_6$ and $R_7$ together are $C_4$-$C_5$alkylene or 3-oxapentalene, and $R_8$ is $C_1$-$C_6$alkyl, $C_5$-$C_6$cycloalkyl, allyl, methallyl, propargyl unsubstituted phenyl or benzyl or phenyl or benzyl which is substituted by $C_1$-$C_4$alkyl, $C_1$-$C_4$alkoxy or halogen, or $R_4$ and $R_5$ taken together are —O— or —NR$_9$— where $R_9$ is unsubstituted $C_1$-$C_6$alkyl or $C_1$-$C_6$alkyl substituted by —OH, —OR$_{12}$ or —SR$_{12}$, wherein $R_{12}$ is $C_1$-$C_6$alkyl, cyclohexyl or phenyl, —COOH, —COOR$_8$, —OCOR$_{12}$, —CONH$_2$, —CONHR$_6$, —CONR$_6$R$_7$, halogen or cyano, or is allyl, methallyl, propargyl unsubstituted phenyl or benzyl or phenyl or benzyl which are substituted by $C_1$-$C_4$alkyl, $C_1$-$C_4$alkoxy or halogen, and with the proviso that $R_4$ is not OH or alkoxy and $R_5$ is not OH, OCH$_3$ or OC$_2$H$_5$ or $R_4$ and $R_5$ together are not —O— when $R_1$ is hydrogen and $R_2$ is methyl.

19. 1-Amino-1,2,3,4-tetrahydropyridine-2,3-dicarboxylic acid derivatives according to claim 18, of the formula IIa

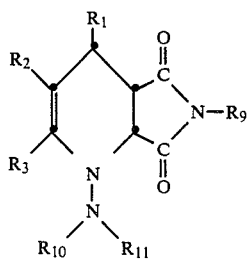

(IIa)

wherein $R_1$, $R_2$, $R_3$, $R_9$, $R_{10}$ and $R_{11}$ have the meanings defined in claim 18.

20. 1,4-Dihydropyridine-2,3-dicarboxylic acid derivatives of the formula III

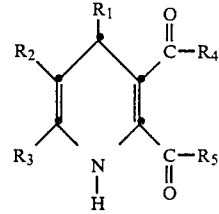

(III)

wherein $R_1$ is hydrogen or $C_1$-$C_6$alkyl, $C_1$-$C_6$alkylthio or $C_1$-$C_6$alkoxy which are unsubstituted or substituted by hydroxy, halogen, $C_1$-$C_4$alkoxy, phenyl, phenoxy, cyano, carboxyl or $C_1$-$C_4$-alkoxycarbonyl; or $R_1$ is phenyl or phenoxy, unsubstituted or substituted by halogen, cyano, $C_1$-$C_4$alkyl, $C_1$-$C_4$alkoxy, $C_1$-$C_4$haloalkyl or $C_1$-$C_4$cyanoalkyl, $R_2$ has the same meaning as $R_1$ and is additionally fluorine, chlorine or bromine, $R_3$ is hydrogen or together with $R_2$ forms a trimethylene or tetramethylene group, $R_4$ and $R_5$ independently of one another are —OH, —NH$_2$, —NHR$_6$, —NR$_6$R$_7$ or —OR$_8$, where $R_6$ and $R_7$ are $C_1$-$C_6$alkyl, $C_5$-$C_6$cycloalkyl, allyl, methallyl, propargyl, unsubstituted $C_6$-$C_{16}$aryl or $C_7$-$C_{16}$aralkyl or $C_6$-$C_{16}$aryl or $C_7$-$C_{16}$aralkyl which are substituted by halogen, cyano, $C_1$-$C_6$alkyl, $C_1$-$C_4$alkoxy, $C_1$-$C_4$haloalkyl or $C_1$-$C_4$cyanoalkyl, or $R_6$ and $R_7$ together are $C_4$-$C_5$alkylene or 3-oxapentalene, and $R_8$ is $C_1$-$C_6$alkyl, $C_5$-$C_6$cycloalkyl, allyl, methallyl, propargyl unsubstituted phenyl or benzyl or phenyl or benzyl which is substituted by $C_1$-$C_4$alkyl, $C_1$-$C_4$alkoxy or halogen, or $R_4$ and $R_5$ taken together are —O— or —NR$_9$— where $R_9$ is unsubstituted $C_1$-$C_6$alkyl or $C_1$-$C_6$alkyl substituted by —OH, —OR$_{12}$ or —SR$_{12}$, wherein $R_{12}$ is $C_1$-$C_6$alkyl, cyclohexyl or phenyl, —COOH, —COOR$_8$, —OCOR$_{12}$, —CONH$_2$, —CONHR$_6$, —CONR$_6$R$_7$, halogen or cyano, or is allyl, methallyl, propargyl unsubstituted phenyl or benzyl or phenyl or benzyl which are substituted by $C_1$-$C_4$alkyl, $C_1$-$C_4$alkoxy or halogen.

21. 1,4-Dihydropyridine-2,3-dicarboxylic acid derivatives according to claim 20, of the formula IIIa

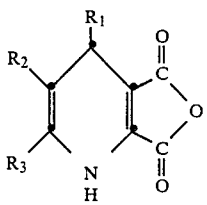

(IIIa)

wherein $R_1$, $R_2$ and $R_3$ have the meanings defined in claim 20.

22. 1,4-Dihydropyridine-2,3-dicarboxylic acid derivatives according to claim 20, of the formula IIIb

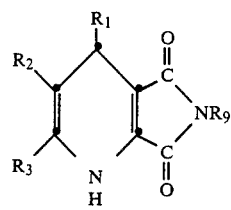
(IIIb)
wherein $R_1$, $R_2$, $R_3$ and $R_9$ have the meanings defined in claim 20.
* * * * *
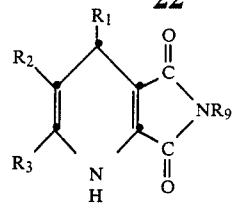
(IIIb)
wherein $R_1$, $R_2$, $R_3$ and $R_9$ have the meanings defined in claim 20.
* * * * *